United States Patent [19]

Harandi

[11] Patent Number: 5,177,279
[45] Date of Patent: Jan. 5, 1993

[54] INTEGRATED PROCESS FOR CONVERTING METHANOL TO GASOLINE AND DISTILLATES

[75] Inventor: Mohsen N. Harandi, Lawrenceville, N.J.

[73] Assignee: Mobil Oil Corporation, Fairfax, Va.

[21] Appl. No.: 769,508

[22] Filed: Oct. 1, 1991

Related U.S. Application Data

[63] Continuation of Ser. No. 601,955, Oct. 23, 1990, abandoned.

[51] Int. Cl.[5] ............................................. C07C 1/20
[52] U.S. Cl. .................................... 585/312; 585/315; 585/316; 585/329; 585/413; 585/415; 585/469; 585/517; 585/640
[58] Field of Search ............... 585/312, 315, 316, 329, 585/330, 413, 415, 517, 518, 533, 469, 717, 640

[56] References Cited

U.S. PATENT DOCUMENTS

| | | | |
|---|---|---|---|
| 3,931,349 | 1/1976 | Kuo | 585/640 |
| 4,404,414 | 9/1983 | Penick et al. | 585/469 |
| 4,482,772 | 11/1984 | Tabak | 585/254 |
| 4,506,106 | 3/1985 | Hsia et al. | 585/312 |
| 4,520,215 | 5/1985 | Owen et al. | 585/255 |
| 4,542,252 | 9/1985 | Graziani et al. | 585/640 |
| 4,547,602 | 10/1985 | Tabak | 585/314 |
| 4,579,999 | 4/1986 | Gould et al. | 585/312 |
| 4,587,373 | 5/1986 | Hsia | 585/639 |
| 4,590,320 | 5/1986 | Sapre | 585/324 |
| 4,654,453 | 3/1987 | Tabak | 585/303 |
| 4,788,365 | 11/1988 | Harendi et al. | 585/312 |
| 4,899,002 | 2/1990 | Harendi et al. | 585/312 |

Primary Examiner—Asok Pal
Attorney, Agent, or Firm—Alexander J. McKillop; Charles J. Speciale; L. G. Wise

[57] ABSTRACT

An integrated process for the conversion of methanol feed to gasoline and distillate range liquid hydrocarbons comprising the steps of splitting the methanol feed into two portions, contacting the first portion of the methanol feed with a medium-pore shape selective zeolite catalyst in a first reaction zone at elevated temperature and moderate pressure to convert the first portion of the methanol feed to hydrocarbons comprising $C_2+$ olefins; cooling and separating effluent from the first reaction zone to recover a $C_3+$ olefin hydrocarbon stream and a $C_2-$ light gas stream; pressurizing the $C_3+$ olefin hydrocarbon stream and the second portion of the methanol feed and contacting the $C_3+$ hydrocarbon stream and the methanol feed in a second reaction zone with a medium-pore shape selective oligomerization zeolite catalyst at substantially increased pressure and moderate temperature to convert at least a portion of the $C_3+$ hydrocarbons and methanol feed to heavier liquid hydrocarbon product stream comprising olefinic gasoline and distillate range liquids.

6 Claims, 4 Drawing Sheets

INTEGRATED PROCESS FOR CONVERTING METHANOL TO GASOLINE AND DISTILLATES

This is a continuation of copending application Ser. No. 07/601,955 filed on Oct. 23, 1990, now abandoned.

BRIEF DESCRIPTION OF THE INVENTION

The present invention relates to an integrated process for the conversion of oxygenates, such as methanol or dimethyl (DME), to liquid hydrocarbons. In particular the invention provides a process which comprises splitting the oxygenate feed into two portions. The first portion of the feed is contacted with a zeolite catalyst in a first reactor at elevated temperature and moderate pressure to obtain a light olefinic product stream. The second portion of the oxygenate feed is fed together with the light olefinic product stream from the first reactor at substantially increased pressure and moderate temperature to a second reactor and contacted with an oligomerization zeolite catalyst to produce heavier liquid hydrocarbons.

In an alternative embodiment of the invention the second portion of the oxygenate feed is fed together with the light olefinic product stream from the first reactor to an intermediate reactor and contacted with a zeolite catalyst at moderate temperature and increased pressure to obtain an olefinic stream rich in $C_4$ to $C_{11}$ olefins.

The olefinic product stream from the intermediate reactor can optionally be fed to the second reactor at substantially increased pressure and moderate temperature and contacted with an oligomerization zeolite catalyst to produce heavier liquid hydrocarbons.

BACKGROUND OF THE INVENTION

In order to provide an adequate supply of liquid hydrocarbons for use as synfuels or chemical feedstocks, various processes have been developed for converting coal and natural gas to gasoline, distillate and lubricants. A substantial body of technology has grown to provide oxygenated intermediates, especially methanol. Large scale plants can convert methanol or similar aliphatic oxygenates to liquid fuels, especially gasoline. However, the demand for heavier hydrocarbons has led to the development of processes for increasing the yield of gasoline and diesel fuel by multi-stage techniques.

Recent developments in zeolite catalysts and hydrocarbon conversion processes have created interest in utilizing olefinic feedstocks, for producing $C_5+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2$-$C_5$ alkenes. This process may supplant conventional alkylation units. In U.S. Pat. No. 3,960,978 and U.S. Pat. No. 4,021,502, Plank, Rosinski and Givens disclose conversion of $C_2$-$C_5$ olefins alone or in admixture with paraffinic components, into higher hydrocarbons over crystalline zeolites having controlled acidity. Garwood et al have also contributed improved processing techniques to the MOGD system, as in U.S. Pat. No. 4,150,062, U.S. Pat. No. 4,211,640 and U.S. Pat. No. 4,227,992. The above-identified disclosures are incorporated herein by reference.

Conversion of lower olefins, especially propene and butenes, over ZSM-5 is effective at moderately elevated temperatures and pressures. The conversion products are sought as liquid fuels, especially the $C_5+$ aliphatic and aromatic hydrocarbons. Olefinic gasoline is produced in good yield by the MOGD process and may be recovered as a product or recycled to the reactor system for further conversion to distillate-range products. Operating details for typical MOGD units are disclosed in U.S. Pat. No. 4,445,031, U.S. Pat. No. 4,456,779, Owen et al, and U.S. Pat. No. 4,433,185, Tabak, incorporated herein by reference.

In addition to their use as shape selective oligomerization catalysts, the medium pore ZSM-5 type catalysts are useful for converting methanol and other lower aliphatic alcohols or corresponding ethers to olefins. Particular interest has been directed to a catalytic process ("MTO") for converting low cost methanol to valuable hydrocarbons rich in ethene and $C_3+$ alkenes. Various processes are described in U.S. Pat. No. 3,894,107 (Batter et al), U.S. Pat. No. 3,928,483 (Chang et al), U.S. Pat. No. 4,025,571 (Lago), U.S. Pat. No. 4,423,274 (Daviduk et al) and U.S. Pat. No. 4,433,189 (Young), incorporated herein by reference. It is generally known that the MTO process can be optimized to produce a major fraction of $C_2$-$C_4$ olefins. Prior process proposals have included a separation section to recover ethene and other gases from by-product water and $C_5+$ hydrocarbon liquids. The oligomerization process conditions which favor the production of $C_{10}$-$C_{20}$ and higher aliphatics tend to convert only a small portion of ethene as compared to $C_3+$ olefins.

The Gould et al U.S. Pat. No. 4,579,999 discloses an integrated process for the conversion of methanol to gasoline and distillate. In a primary catalytic stage (MTO) methanol is contacted with zeolite catalyst to produce $C_2$-$C_4$ olefins and $C_5+$ hydrocarbons. In a secondary catalytic stage (MOGD) containing an oligomerization catalyst comprising medium-pore shape selective acidic zeolite at increased pressure, a $C_3+$ olefins stream from the primary stage is converted to gasoline and/or distillate liquids.

The Harandi et al U.S. Pat. No. 4,899,002 discloses a process for the increased production of olefinic gasoline, which comprises the integration of oxygenates to olefin conversion with olefin to gasoline conversion under moderate severity conditions. The product of the olefins to gasoline conversion is passed to an olefin to gasoline and distillate (MOGD) conversion zone for distillate production.

The methanol to olefin process (MTO) operates at high temperature and moderate pressure and high catalyst severity in order to obtain efficient conversion of the methanol to olefins. These process conditions, however, produce an undesirable amount of aromatics and $C_2-$ olefins and require a large investment in plant equipment.

The olefins to gasoline and distillate process (MOGD) operates at moderate temperatures and elevated pressures to produce olefinic gasoline and distillate products. When the conventional MTO process effluent is used as a feed to the MOGD process, the aromatic hydrocarbons produced in the MTO unit are desirably separated and a relatively large volume of MTO product effluent has to be cooled and treated to separate a $C_2-$ light gas stream, which is unreactive, except for ethene which is reactive to only a small degree, in the MOGD reactor, and the remaining hydrocarbon stream has to be pressurized to the substantially higher pressure used in the MOGD reactor.

The problems to be solved were to reduce the overal size and investment in the MTO reactor, reduce the amount of the methanol feed fed to the MTO reactor in order that the process could be carried out under lower severity operating conditions which improves selectivity to not produce aromatics and not produce large amounts of $C_2-$ light gas. At the same time it was desired to maintain the total effective amount of the methanol feed converted to olefins and to improve the overal selectivity of the MTO/MOGD process to produce more olefinic gasoline and distillates.

OBJECTS OF THE INVENTION

It is an object of the present invention to improve the overall operation and cost of conversion of methanol to gasoline and distillate by process integration of a methanol to olefin conversion process with an olefin to gasoline and distillate conversion process.

It is another object of the present invention to reduce the size and investment in the methanol to olefin conversion process by splitting the methanol feed between the methanol to olefin conversion step and an olefin to gasoline or distillate conversion step.

SUMMARY OF THE INVENTION

In accordance with the present invention methanol, dimethyl ether (DME) or the like may be converted to liquid fuels, particularly gasoline and distillate, in a continuous process with integration between major process units. The methanol feed is split between two major process units, with a first portion of the methanol feed being fed to the methanol to olefins unit reactor (MTO) and a second portion of the methanol feed being fed to an olefin to gasoline and distillate unit reactor (MOGD) to produce gasoline or distillate.

Alternatively, the second portion of the methanol feed can be fed to an intermediate olefin to gasoline unit reactor (MOI) to produce gasoline.

Another alternative is to take the gasoline effluent from the intermediate reactor (MOI) and feed it to the olefin to gasoline and distillate reactor (MOGD) to produce distillate.

The present invention is specifically directed to an integrated process for the conversion of oxygenate feeds such as methanol and dimethyl ether to olefinic gasoline and distillate range liquid hydrocarbons. The process comprises the steps of splitting the methanol feed into two portions, contacting the first portion with zeolite catalyst in a first reactor at elevated temperature and moderate pressure to convert the methanol to $C_2+$ light olefin hydrocarbons. The effluent from first reactor is cooled to separate a $C_2+$ or $C_3+$ olefin hydrocarbon stream and a $C_2-$ hydrocarbon stream.

The $C_2+$ or $C_3+$ olefin hydrocarbon stream and the second portion of the methanol feed are pressurized and contacted in a second reactor with oligomerization catalyst at substantially increased pressure and moderate temperature to convert the $C_2+$ or $C_3+$ olefin stream and methanol to a heavier liquid hydrocarbon stream comprising olefinic gasoline and distillate range hydrocarbons. The heavier liquid stream is cooled to preliminarily separate $C_3+$ liquid hydrocarbons from $C_2-$ light gas and by-product water. The $C_2-$ light gas can be recycled to the first reactor or removed for further processing. The $C_3+$ liquid hydrocarbons can be further treated to recover an LPG stream, a $C_5-C_9$ olefinic gasoline stream and a $C_{10}$ to $C_{20}$ distillate stream.

In an other embodiment of the invention the second portion of the methanol feed is fed to an intermediate reactor in which it is mixed with an olefinic hydrocarbon effluent stream from the first reactor and contacted with a zeolite catalyst at moderate temperatures and increased pressures to produce an olefinic gasoline boiling range hydrocarbon product effluent.

In another embodiment of the invention the olefinic gasoline boiling range hydrocarbon product effluent from the intermediate reactor is pressurized and contacted in a second reactor with oligomerization catalyst at substantially increased pressure and moderate temperature to convert the olefinic gasoline boiling range hydrocarbons to a heavier liquid hydrocarbon stream comprising olefinic gasoline and distillate range hydrocarbons.

The heavier liquid stream is cooled to preliminarily separate $C_3+$ liquid hydrocarbons from $C_2-$ light gas and water. The $C_2-$ light gas can as before be recycled to the first reactor and the $C_3+$ liquid hydrocarbons can be further treated to recover a LPG stream, a $C_5-C_9$ olefinic gasoline stream and a $C_{10}$ to $C_{20}$ distillate stream.

Advantageously the first and second reactor as well as the intermediate reactor can contain ZSM-5 type zeolite catalyst.

DETAILED DESCRIPTION OF THE INVENTION

Oxygenated Feed

Numerous oxygenate organic compounds can be used as the feed to be converted to olefinic gasoline and distillate in the present invention. Since methanol or its ether derivative (DME) are industrial commodities from synthesis gas or the like processes, these materials are utilized in the description herein as preferred starting materials. It is understood by those skilled in the art that the methanol to olefin (MTO) type processes can employ methanol, dimethyl ether and mixtures thereof, as well as other lower aliphatic alcohols and ethers, lower ketones and/or oldehydes. It is also understood by those skilled in the art to partially convert oxygenates, such as methanol, by dehydration, as in the catalytic reaction of methanol over gamma-alumina to produce DME intermediate. Typically, an equilibrium mixture ($CH_3OH \rightleftharpoons CH_3OCH_3 + H_2O$) is produced by partial dehydration. This reaction takes place in the first reactor, methanol to lower olefins (MTO); in the intermediate reactor, methanol and olefins to olefinic gasoline (MOI); and in the second reactor, methanol and olefins to gasoline and distillate (MOGD).

Catalyst

Catalyst versatility permits the same zeolite catalyst to be used in the first reactor unit (MTO) and second reactor unit oligomerization stage (MOGD), as well as in the intermediate reactor unit. While it is within the inventive concept to employ substantially different catalysts in these reactors, it is advantageous to employ a standard ZSM-5 having a silica alumina molar ratio of 70:1 in the first, intermediate and second reactors.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 structures may be utilized by employing highly siliceous material or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The zeolite catalysts preferred for use herein include the medium pore (i.e., about 5-7 A) shape-selective crystalline aluminosilicate zeolites having a silica-to-alumina ratio of at least 12, a constraint index of about 1 to 12 and acid cracking activity of about 1-200. In an operating reactor the coked catalyst may have an apparent activity (alpha value) of about 1 to 80 under the process conditions to achieve the required degree of reaction severity. Representative of the ZSM-5 type zeolites are ZSM-5, ZSM-11, ZSM-12, ZSM-22, ZSM-23, ZSM-35, ZSM-38 and MCM-22. ZSM-5 is disclosed in U.S. Pat. No. 3,702,886 and U.S. Pat. No. Re. No. 29,948. The ZSM-5, ZSM-12, ZSM-22, ZSM-23, and ZSM-35 catalyst are preferred. The MCM-22 catalyst is described in U.S. Pat. No. 4,954,325. Other suitable zeolites are disclosed in U.S. Pat. No. 3,709,979, U.S. Pat. No. 3,832,449, U.S. Pat. No. 4,076,979, U.S. Pat. No. 4,076,842, U.S. Pat. No. 4,016,245 and U.S. Pat. No. 4,046,839, U.S. Pat. No. 4,414,423, U.S. Pat. No. 4,417,086, U.S. Pat. No. 4,517,396 and U.S. Pat. No. 4,542,251. The disclosures of the above mentioned patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1. A typical zeolite catalyst component having Bronsted acid sites may consist essentially of aluminosilicate ZSM-5 zeolite with 5 to 95 wt. % silica and/or alumina binder.

Certain of the ZSM-5 type medium pore shape selective catalysts are sometimes known as pentasils. In addition to the preferred aluminosilicates, the borosilicate, ferrosilicate and "silicalite" materials may be employed. It is advantageous to employ a standard ZSM-5 having a silica:alumina molar ratio of 25:1 to 70:1 with an apparent alpha value of 1-80. ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred. The zeolite catalyst crystals are normally bound with a suitable inorganic oxide, such as silica, alumina, etc. to provide a zeolite concentration of about 5 to 95 wt. %. A preferred catalyst comprises 25% to 65% HZSM-5 catalyst contained within a silica-alumina matrix binder and having a fresh alpha value of less than 500.

When employing a ZSM-5 type zeolite catalyst in a fluidized bed as a fine powder such a catalyst should comprise the zeolite suitably bound or impregnated on a suitable support with a solid density (weight of a representative individual particle divided by its apparent "outside" volume) in the range from 0.6-2 g/cc, preferably 0.9-1.6 g/cc. The catalyst particles can be in a wide range of particle sizes up to about 250 microns, with an average particle size between 20 and 100 microns, preferably in the range of 10-150 microns and with the average particle size between 40 and 80 microns. When these solid particles are placed in a reactor bed where the superficial fluid velocity is 0.3-2 ft./sec., fluidized bed operation is obtained. The velocity specified here is for an operation at a total reactor pressure of about 0 to 30 psig (100 to 300 kPa). Those skilled in the art will appreciate that at higher pressures, a lower gas velocity may be employed to ensure fluidized bed operation.

In the fluidized bed embodiments of the present invention it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt. % of the total catalyst in the reaction zone in the size range less than 32 microns. This class of fluidizable particles is classified as Geldart Group A.

The light olefin production is promoted by the zeolite catalysts having a high concentration of Bronsted acid reaction sites. Accordingly, an important criterion is selecting and maintaining the catalyst to provide either fresh catalyst having acid activity or by controlling catalyst deactivation and regeneration rates to provide an apparent average alpha value of about 1 to 50, preferably 1 to 10.

A further description of the zeolite catalyst is found in Owen et al U.S. Pat. No. 4,456,779 which is incorporated herein by reference.

The oligomerization catalysts preferred for use herein in the MOGD fixed bed reactor include the crystalline aluminosilicate zeolites having a silica to alumina ratio of at least 12, a constraint index of about 1 to 12 and acid cracking activity of about 160-200. A suitable catalyst for fixed bed operation is 65 wt. % HZSM-5 zeolite with an alumina binder in the form of cylindrical extrudates of about 1-5 mm. Other catalysts and processes suitable for converting methanol/DME to lower olefins are disclosed in U.S. Pat. No. 4,393,265 (Bonafaz), U.S. Pat. No. 4,387,263 (Vogt et al) and European Patent Application No. 0081683 (Marosi et al).

The ZSM-5 type catalysts are particularly advantageous for use in the present invention because the same material may be employed for dehydration of methanol to DME, conversion of methanol to lower olefins and oligomerization reactions. A particular advantage of the process of the present invention is that the spent catalyst from a higher pressure unit can be used in a lower pressure unit as fresh make-up catalyst.

REACTORS

A number of different types of reactors can be used in the above mentioned processes, including tubular, moving bed, fixed bed, fluid bed and riser reactors. The preferred reactor types and the operations of each in the processes are briefly described below.

MTO Reactor I

The MTO reaction is preferably carried out in a fluidized bed reactor because of the highly exothermic nature of the methanol to olefin reaction. In a preferred MTO reactor, a bed of finely divided (150 microns) ZSM-5 catalyst is maintained in a turbulent fluidization regime. Hot feedstock vapor is passed upwardly through the fluidized bed at a superficial velocity of about 0.3 to 2 meters per second, maintaining a bed density of about 200 to 600 kg/m$^3$. By operating at about 520° C.+20° C. and a catalyst activity sufficient to yield a propane:propene ratio of about 0.02 to 0.3:1, the production of ethylene can be controlled at a low level.

A suitable reactor and operating technique for carrying out this step of the invention are disclosed in Gould et al Ser. No. 687,045, filed Dec. 28, 1984. Other fluidized bed reactor systems suitable for use in the MTO reactor stage are disclosed in Avidan U.S. Pat. No. 4,746,762 and Harandi et al U.S. Pat. No. 4,777,316, both of which are incorporated herein by reference.

Though fluidized bed reactors are preferred for the MTO reactor stage, multi-stage fixed bed reactors provided with inter-stage cooling can also be used. See, for example, Graziani et al U.S. Pat. No. 4,542,252.

MOI Intermediate Reactor A

The MOI reaction is preferably carried out in a fluidized bed reactor because of the highly exothermic nature of the methanol to olefins reaction. Accordingly, the fluidized bed reactor systems described with regard to the MTO reactor I can be adapted for carrying out this process step.

In addition to the fluidized bed and fixed bed reactor systems described with regard to the MTO reactor I, in certain circumstances the multi-stage fixed bed reactor systems described below with regard to the MOGD reactor II can be used in the MOI reaction.

MOGD Reactor II

The MOGD reaction is preferably carried out in a fixed bed multi-stage reactor. Suitable reactor designs, process conditions and techniques are described in Harandi et al U.S. Pat. No. 4,777,316, Harandi et al U.S. Pat. No. 4,877,921, Gould U.S. Pat. No. 4,579,999 and Owen et al U.S. Pat. No. 4,456,779, all of which are incorporated herein by reference thereto.

Though a fixed bed multi-stage reactor is preferred for the MOGD reaction system, in certain circumstances a fluidized bed reactor system can be used. For example, see Harandi et al U.S. Pat. No. 4,877,921 which is incorporated herein by reference thereto.

In the description used in the present application, metric units and parts by weight are employed unless otherwise stated. Various reactor configurations may be used, including fluidized bed catalytic reactors, moving bed and multi-stage fixed bed reactors.

The invention is further described with reference to the figures of the drawings.

DESCRIPTION OF THE FIGURES OF THE DRAWINGS

Figure 1:
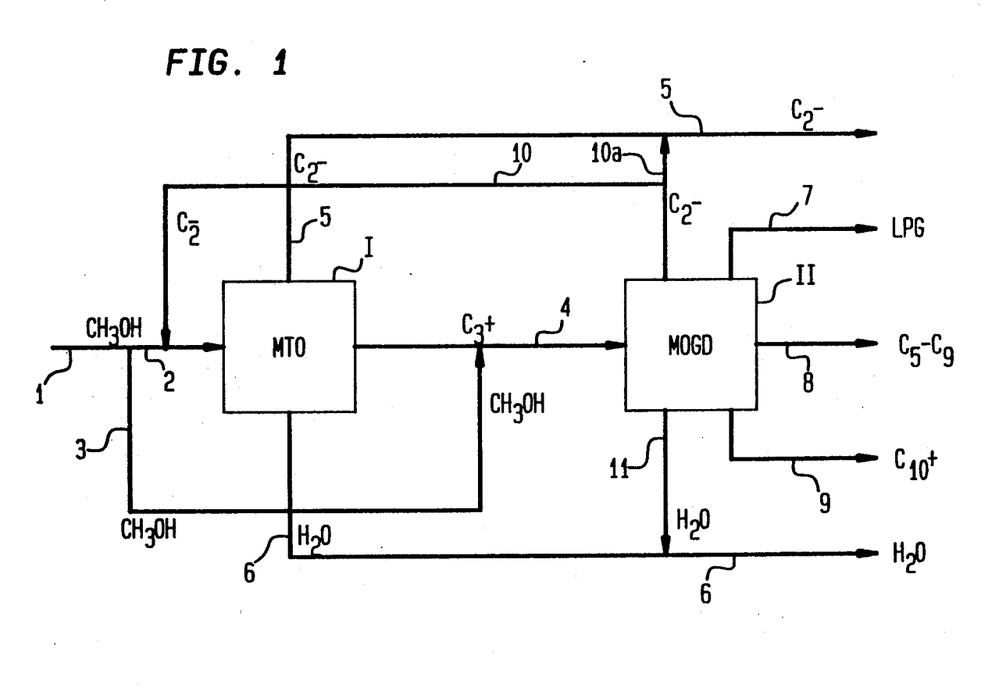
FIG. 1 is a process flow sheet showing the integration of the methanol to olefins (MTO) unit reactor and the olefins to gasoline and distillate (MOGD) unit reactor operations and the process streams.

Referring to FIG. 1 methanol feed in line 1 is split with a first portion being fed to line 2 and a second portion being fed to line 3. The methanol feed can contain 0 to 50% by weight water, generally 5 to 40% by weight water, typically 4 to 20% by weight water. Preferably the methanol feed contains less than 5% by weight water. The first portion of the methanol feed in line 2 can be 10 to 90%, preferably 40 to 60%, and more preferably about 45 to 55% of the total methanol feed and is fed through line 2 to the MTO reactor I. The second portion of the methanol feed in line 3 can be 90 to 10%, preferably 60 to 40% and more preferably 55 to 45% of the total methanol feed and is fed through lines 3 and 4 to the MOGD reactor II.

The first portion of methanol feed fed through line 1 can be mixed in line 2 with recycle ethene fed through recycle line 10 and contacted in reactor I with HZSM-5 catalyst where the methanol is converted to lower olefins and gasoline and by-product water. The water is formed by the dehydration of the methanol.

The methanol is fed to reactor I at 0.2 to 200 WHSV, preferably 0.3 to 3 WHSV and more preferably 0.5 to 2 WHSV. The recycle ethene is fed to reactor I at 0 to 100 WHSV, preferably 0 to 5 WHSV, and more preferably at 0 to 1 WHSV. The reactor I is operated as a dense fluidized bed at elevated temperatures of 260° to 538° C. (500° to 1000° F.), preferably 427° to 510° C. (800° to 950° F.), and more preferably 471° to 504° C. (880° to 940° F.). The reactor I is operated at moderate pressures of 101 to 652 kPa (0 to 80 psig), preferably 170 to 652 kPa (10 to 80 psig) and more preferably 239 to 308 kPa (20 to 30 psig). The reactor I effluent is cooled by means not shown and the by-product water is recovered by phase separation and withdrawn through line 6.

After separation of water, the reactor I hydrocarbon effluent has the following composition.

|  | Typically Wt. % |
|---|---|
| $C_2-$ | 10–14 |
| $C_3-C_4$ | 45–55 |
| $C_5-C_9$ | 25–35[1] |
| $C_{10}-C_{20}$ | 0–5 |

[1]Aromatics content of gasoline fraction is 10–14 wt. %, based on total hydrocarbons.

At least 70 wt. % and preferably at least 99.9 wt. % of the methanol feed is converted to olefin hydrocarbons.

The effluent hydrocarbons are treated to separate an overhead $C_2-$ gas stream which is withdrawn through line 5 and a liquid $C_3+$ olefin hydrocarbon stream which is withdrawn through line 4. The $C_3+$ olefin stream in line 4 is mixed with the second portion of the methanol feed fed through line 3 and the mixture is fed through line 4 to the MOGD reactor II. The second portion of the methanol and the $C_3+$ olefin effluent from the reactor I are fed to reactor II at 0.01 to 10 WHSV, preferably 0.1 to 5.0 WHSV and more preferably at 0.3 to 1.0 WHSV. The mixed methanol and $C_3+$ olefin hydrocarbon feed is contacted in reactor II with an HZSM-5 catalyst arranged in a multistage fixed bed reactor preferably having three stages. Prior to entering the reactor II the mixed feed is pressurized by means not shown to the substantially increased pressure of the reactor II.

The reactor II is operated at a temperature of 177° to 371° C. (350° to 700° F.), preferably 204° to 343° C. (400° to 650° F.) and more preferably 204° to 316° C. (400° to 600° F.). The reactor II is operated at a pressure of 4237 to 20,780 kPa (600 to 3000 psig), preferably 4237 to 10,440 kPA (600 to 1500 psig) and more preferably 5600 to 7000 kPa (800 to 1000 psig). At the lower pressures gasoline products are selectively produced, while at the higher pressures lubricating oil stocks are selectively produced.

After separation of any unconverted methanol and water that may be present, the reactor II hydrocarbon effluent has the following composition.

|  | Typically Wt. % |
|---|---|
| $C_2-$ | 1-2 |
| $C_3-C_4$ | 8-12 |
| $C_5-C_9$ | 15-30[1] |
| $C_{10}-C_{20}$ | 60-75 |

[1]Aromatics content of gasoline fraction is 0-12 wt. %, based on total hydrocarbons. Normally aromatics are separate from the reactor I effluent in which case there would be none present since aromatics are not produced in the MOGD reactor II.

At least 70% and preferably at least 95% of the methanol feed is converted to olefin hydrocarbons.

The reactor II effluent is separated by means not shown into a $C_2-$ light gas withdrawn through line 10 which may optionally be recycled to reactor I or removed from the system through lines 10a and 5; a gas stream comprising $C_3-C_4$ (LPG) hydrocarbons is withdrawn through line 7; a $C_5$ to $C_9$ olefinic gasoline stream is withdrawn through line 8; and a $C_{10}-C_{20}$ distillate hydrocarbon stream is withdrawn through line 9. The water present is separated by cooling and phase separation and is withdrawn through line 11. The $C_2$ light gas comprises ethane, ethene, methane and hydrogen.

The lower pressures increase the selectivity to gasoline hydrocarbons, while the higher pressures increase selectivity to distillate hydrocarbons. At any particular selected pressure the higher temperatures, for example, 371° to 538° C. (700° to 1000° F.), preferably 371° to 482° C. (700° to 900° F.) and more preferably 371° to 427° C. (700° to 800° F.), increase selectivity to gasoline, while the lower temperatures 260° to 371° C. (500° to 700° F.), preferably 288° to 343° C. (550° to 650° F.) and more preferably 316° to 343° C. (600° to 650° F.), increase selectivity to distillate.

Figure 2:
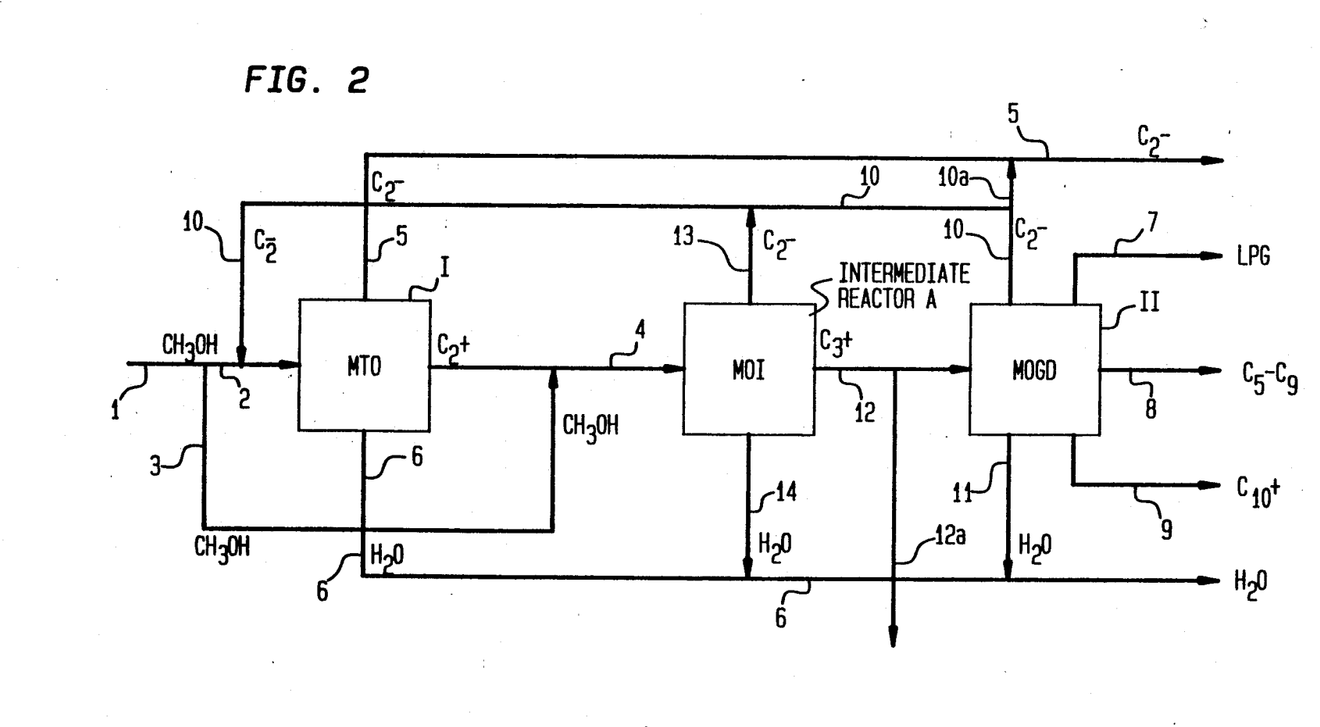
FIG. 2 is a process flow sheet showing the integration of the methanol to olefins (MTO) unit reactor, the olefins to olefinic gasoline (MOI) unit reactor and the olefins to gasoline and distillate (MOGD) unit reactor operations and process streams.

The FIG. 2 of the drawings illustrates an alternative process design in which an intermediate MOI (olefin interconversion) reactor is placed between the MTO reactor I and the MOGD reactor II. The overall process conditions of the FIG. 2 drawing are similar to those described with regard to FIG. 1 with the exception that the second portion of the methanol feed is fed to the intermediate reactor A together with the effluent hydrocarbon stream from the reactor I.

The methanol feed is fed through line 1 and is split into a portion fed to line 2 and a second portion fed to line 3. The first portion of the methanol feed in line 2 can be 10 to 90%, preferably 40 to 60% and more preferably about 45-55% of the total methanol feed and is fed through line 2 to the MTO reactor I. The second portion of the methanol feed in line 3 can be 90 to 10%, preferably 60 to 40% and more preferably 45 to 55% of the total methanol and is fed through line 3 to the MOI intermediate reactor A.

The first portion of methanol feed together with recycle ethene fed through recycle line 10 is contacted in reactor I with HZSM-5 catalyst where the methanol is converted to lower olefins and light gasoline and by-product water. The methanol is fed to reactor I at 0.2 to 200 WHSV, preferably 0.3 to 3 WHSV and more preferably 0.5 to 2 WHSV. The recycle ethene is optional and is fed to reactor I at 0 to 100 WHSV, preferably 0 to 5 WHSV, and more preferably at 0 to 1 WHSV.

The reactor I is operated as a dense fluidized bed at elevated temperatures of 260° to 538° C. (500° to 1000° F.), preferably 427° to 510° C. (800° to 950° F.) and more preferably 471° to 504° C. (880° to 940° F.). The reactor I is operated at moderate pressures of 101 to 652 kPa (0 to 80 psig), preferably 170 to 652 kPa (10 to 80 psig) and more preferably at 239 to 308 kPa (20 to 30 psig).

The reactor I effluent is cooled by means not shown and the by-product water is recovered by phase separation and withdrawn through line 6.

After separation of water, the reactor I hydrocarbon effluent has the following composition.

|  | Typically Wt. % |
|---|---|
| $C_2-$ | 10-14 |
| $C_3-C_4$ | 45-55 |
| $C_5-C_9$ | 25-35[1] |
| $C_{10}-C_{20}$ | 0-5 |

[1]Aromatics content of gasoline fraction is 10-14 wt. %, based on total hydrocarbons.

At least 70% and preferably at least 99.9% of the methanol feed is converted to olefin hydrocarbons.

The separated hydrocarbons are treated to separate an overhead $C_2-$ gas stream which is withdrawn through line 5 and a liquid $C_2+$ olefin hydrocarbon stream which is withdrawn through line 4. The $C_2+$ olefin stream in line 4 is mixed with the second portion of the methanol feed fed through line 3 and the mixture is fed through line 4 to the MOI intermediate reactor A.

The second portion of the methanol and the $C_2+$ olefin effluent from the reactor I are fed to reactor A at 0.01 to 100 WHSV, preferably 0.1 to 20 WHSV, and more preferably at 0.4 to 4 WHSV.

The mixed methanol and $C_2+$ olefin hydrocarbons are contacted in reactor A with an HZSM-5 catalyst preferably arranged in a dense fluidized bed reactor.

The intermediate reactor A is operated at a temperature of 260° to 538° C. (500° to 1000° F.), preferably 288° to 371° C. (550° to 700° F.) and more preferably 316° to 343° C. (600° to 650° F.). The reactor A is operated at a pressure of 100 to 5616 kPa (0 to 800 psig), preferably 790 to 1824 kPa (100 to 250 psig) and more preferably 1000 to 1480 kPa (130 to 200 psig).

After the separation of any water and unconverted methanol that may be present, the reactor A hydrocarbon effluent has the following composition.

|  | Typically Wt. % |
|---|---|
| $C_2-$ | 1-7 |
| $C_3-C_4$ | 5-15 |
| $C_5-C_9$ | 35-70[1] |
| $C_{10}-C_{20}$ | 5-35 |

[1]The aromatics content of gasoline fraction is 0-15 wt. %, based on total hydrocarbons. Normally aromatics are separated from the reactor I effluent in which case there would be none present since no appreciable amount of aromatics are produced in the MOI intermediate reactor A.

At least 70% and preferably at least 95% of the methanol is converted to olefin hydrocarbons.

The intermediate reactor A effluent is separated by means not shown into a $C_2-$ olefin stream withdrawn through line 13 through which all or a part may be recycled through lines 13 and 10 to reactor I, or removed for further treatment through line 10a, a $C_3+$ olefinic stream withdrawn through line 12, and a by-product water stream withdrawn through line 14.

In the embodiment of the invention where it is desired to increase selectivity to gasoline range hydrocarbons, the $C_3+$ light hydrocarbon stream in line 12 is recovered through line 12a as the product of the process.

In the embodiment of the invention where it is desired to increase selectivity to distillate range hydrocarbons the $C_3+$ light hydrocarbon stream in line 3 is fed through line 12 to the MOGD reactor II.

The $C_3+$ stream is fed to reactor II at 0.01 to 10 WHSV, preferably 0.1 to 5.0 WHSV and more preferably 0.3 to 1.0 WHSV.

Any unconverted methanol in the reactor A effluent is essentially in streams 12 and 14. The unconverted methanol in stream 14 can be distilled alone or with any other aqueous stream containing methanol and the recovered methanol feed to reactor II. Obviously any unconverted methanol in stream 12 is feed to reactor II. The reactor A effluent $C_3+$ stream is contacted in reactor II with an HZSM-5 catalyst arranged in a multi-stage fixed bed reactor having three stages. Prior to entering the reactor II the $C_3+$ stream feed is pressurized by means not shown to the substantially increased pressure of the reactor II.

The reactor II is operated at an outlet temperature of 177° to 371° C. (350° to 700° F.), preferably 204° to 343° C. (400° to 650° F.) and more preferably 204° to 316° C. (400° to 600° F). The reactor II is operated at a pressure of 4237 to 20,780 kPa (600 to 3000 psig), preferably 4237 to 10,440 kPa (600 to 1500 psig) and more preferably 5600 to 7000 kPa (800 to 1000 psig).

After the separation of any water and unconverted methanol that may be present, the reactor II hydrocarbon effluent has the following composition.

|  | Typically Wt. % |
| --- | --- |
| $C_2-$ | 0–3 |
| $C_3-C_4$ | 5–12 |
| $C_5-C_9$ | 20–60[1] |
| $C_{10}-C_{20}$ | 20–65 |

[1] The aromatics content of gasoline fraction is 0–15 wt. %, based on total hydrocarbons. Normally aromatics are separated from the reactor I effluent in which case there would be none present since no appreciable amount of aromatics are produced in the MOI intermediate reactor A.

At least 50% and preferably at least 70% of the $C_3+$ olefin stream is converted to higher hydrocarbons.

The reactor II effluent is separated by means not shown into a $C_2-$ light gas stream withdrawn through line 10 which is optionally recycled to reactor I; a light liquid stream comprising $C_3-C_4$ (LPG) hydrocarbons withdrawn through line 7; a $C_5$ to $C_9$ olefin gasoline stream withdrawn through line 8, and a $C_{10}-C_{20}$ distillate hydrocarbon stream withdrawn through line 9.

At the higher pressures a substantial amount of $C_{20}+$ hydrocarbons are obtained which can be hydrotreated and used as lubricant stock. Any water present is separated by cooling and phase separation and is withdrawn through line 11. In the event there is any appreciable amounts of unconverted methanol present in streams 7 and/or 8, the streams can be washed with water to eliminate methanol in these streams and the recovered methanol can be recycled.

The relative proportion of $C_5-C_9$ gasoline and $C_{10}-C_{20}$ distillate is determined by the reaction conditions in reactor II. The higher temperatures and lower pressures favor the $C_5-C_9$ gasoline production and the lower temperatures, higher pressures and gasoline recycle favor heavy $C_{10}-C_{20}$ distillate production. The $C_5-C_9$ gasoline fraction withdrawn through line 8 can optionally be recycled by means not shown to the MOGD reactor II to increase the production of distillate.

The present invention is illustrated by the following examples.

EXAMPLE 1

Figure 3:
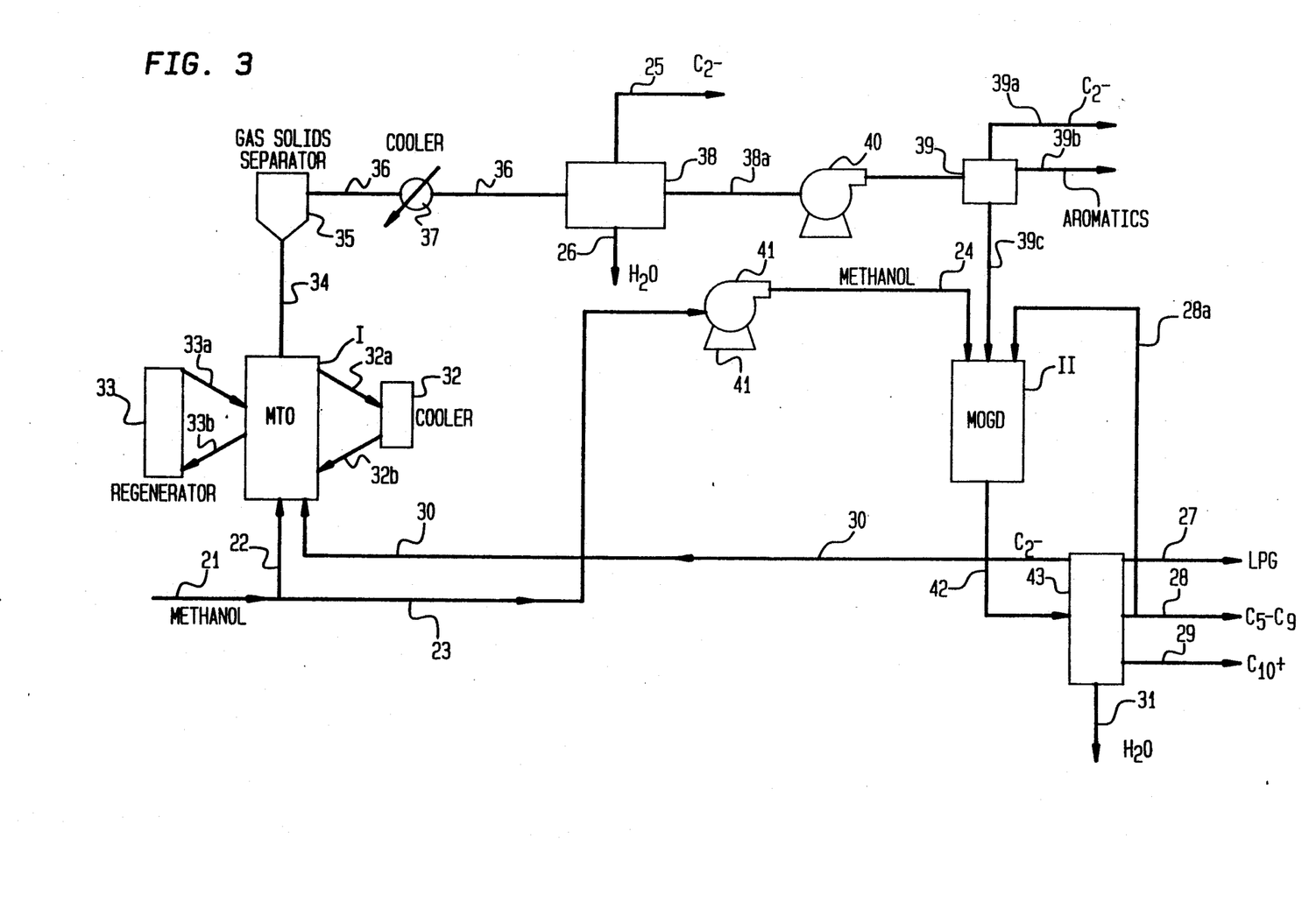
FIG. 3 is a detailed illustration of a preferred integrated process of the FIG. 1 operation.

This example is described with reference to FIG. 3 of the drawings. The FIG. 3 is a schematic flow sheet of the process of the present invention. A liquid methanol feed containing less than 5% water, preferably less than 1% water is heated by means not shown and fed into line 21. The methanol fed is split into a first portion fed to line 22 and a second portion fed to line 23. The first portion contains about 50% of the methanol fed and is fed through line 22 to the fluid bed MTO reactor I. An ethene rich stream is separated from the MOGD reactor II effluent and can optionally be recycled through line 30 to the MTO reactor I and fed to Reactor I with the methanol feed. The methanol is fed at a 0.5 to 2 WHSV and no recycle ethene is fed, i.e. recycle ethene is 0 WHSV.

The MTO fluid bed reactor I is operated in the preferred turbulent dense bed mode. Exothermic heat of reaction is removed in an external cooling vessel 32 by circulating catalyst through transfer lines 32a and 32b in a conventional manner. The catalyst is HZSM-5 and is circulated continuously to the catalyst regenerator vessel 33 through transfer lines 33a and 33b.

The fluid bed catalyst contains 15–30% ZSM-5 and the remainder alumina and/or silica carrier. The particle size distribution contains more than 97% 10 microns and larger. The alpha cracking value of the equilibrated catalyst is preferably 1–10. The regenerated catalyst coke content is preferably less than 0.1 wt. %. The catalyst regeneration temperature in regenerator 33 is controlled at 850° to 990° F., preferably by internal cooling coils.

The reactor I is operated at a temperature of 482° to 527° C. (900° to 980° F.) and at a pressure of 170 to 273 kPa (10 to 25 psig). The MTO product gas is withdrawn from the reactor I by line 34 and separated from any entrained catalyst in gas/solids separator 35. The effluent product gas is taken through line 36, cooled by cooler 37 and is separated in separation vessel 38 into a by-product water stream withdrawn through line 26, $C_2-$ light hydrocarbon gas stream withdrawn through line 25 and a $C_3+$ liquid hydrocarbon stream withdrawn through line 38a.

After separation of the water and any unconverted methanol in separation vessel 38, the hydrocarbon effluent in line 38a has the following composition.

|  | Wt. % |
| --- | --- |
| $C_2-$ | 12 |
| $C_3-C_4$ | 52 |
| $C_5-C_9$ | 33[1] |

| | Wt. % |
|---|---|
| C$_{10}$-C$_{20}$ | 3 |

[1] The aromatic content of the gasoline fraction is 12 wt. %, based on total hydrocarbons.

The methanol conversion to olefins is about 99.8%.

The MOGD reactor is operated in the distillate mode. The C$_3$+ hydrocarbons are fed through line 38a to pump 40 in which the pressure of the hydrocarbons is increased to 5600 to 7000 kPa (800 to 1000 psig) and fed to separation means 39. In separation means 39 an everhead C$_2$− stream is removed through line 39a and a C$_5$-C$_9$ aromatics stream is removed through line 39b. The remaining C$_3$+ olefin hydrocarbons are removed through line 39c and are fed to the MOGD reactor II. The second portion of the methanol feed comprising about 50% of the original methanol feed is fed through line 23 to pump 41 and increased in pressure to 5600 to 7000 kPa (800 to 1000 psig) and fed through line 24 to the MOGD reactor II. The feed rate of the combined C$_3$+ hydrocarbon stream in line 39 and the methanol stream in line 24 to the MOGD reactor II is 0.3 to 1.0 WHSV. The reactor II feed includes a 1:1 weight ratio of recycle of the C$_5$-C$_9$ stream which is fed through lines 28 and 28a.

The methanol and C$_3$+ olefin hydrocarbons are mixed in the reactor II and contacted with HZSM-5 catalyst in a multi-stage fixed bed reactor having three stages. The reactor II is operated under conditions to optimize distillate product at a pressure of 5600 to 7000 kPa (800 to 1000 psig) and at a temperature of 204° to 316° C. (400° to 600° F.). A portion or all of the C$_5$-C$_9$ fraction withdrawn through line 28 is recycled in the embodiment in which the MOGD reactor is operated in the distillate mode.

The reactor II effluent hydrocarbon product is withdrawn through line 42, cooled by means not shown and is fed to separation means 43. After separation of any water and unconverted methanol that may be present through line 31, the reactor II hydrocarbon effluent has the following composition.

| | Wt. % |
|---|---|
| C$_2$− | 1.0 |
| C$_3$-C$_4$ | 7.0 |
| C$_5$-C$_9$ | 29[1] |
| C$_{10}$-C$_{20}$ | 63 |

[1] The aromatic content of the gasoline fraction is less than 1 wt. %, based on the total hydrocarbons.

The methanol conversion to olefins is about 98%.

The C$_2$− hydrocarbons as mentioned above can optionally be recycled to the MTO reactor I or all or a portion of them can be removed for ethene recovery. The C$_3$+ hydrocarbon stream is fractionated in a conventional manner with the C$_3$-C$_4$ (LPG) being removed through line 27; the C$_5$-C$_9$ olefin gasoline being removed through line 28; and the C$_{10}$-C$_{20}$ distillate stream being removed through line 29.

EXAMPLE 2

Figure 4:
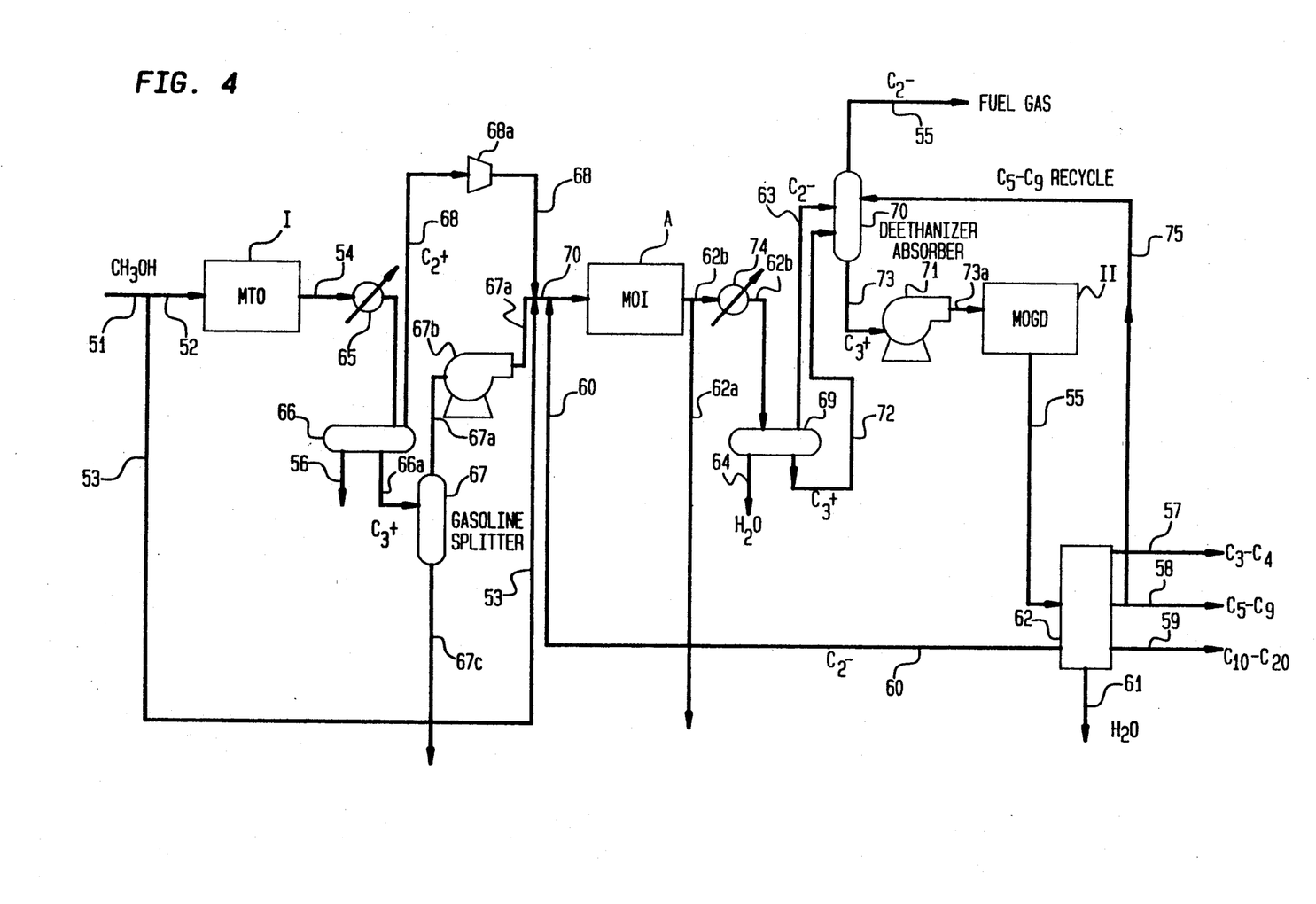
FIG. 4 is a detailed illustration of a preferred integrated process of the FIG. 2 operation.

This example is described with reference to FIG. 4 of the drawings. The FIG. 4 is a schematic flow sheet of a preferred embodiment of the process of the present invention. The FIG. 4 of the drawings illustrates an alternative process design similar to that shown in FIG. 2 in which intermediate MOI (olefin interconversion) reactor A is placed between the MTI reactor I and the MOGD reactor II. The overall process conditions of the FIG. 4 embodiment are similar to those described with regard to FIG. 3 with the exception that the second portion of the methanol feed is fed to the intermediate reactor A together with the effluent hydrocarbon stream from the reactor I. Similar to FIG. 3 a portion of the MOGD reactor II product gasoline can be recycled to the MOGD reactor.

Where the process is carried out to selectively produce gasoline boiling range hydrocarbons only the first two steps are used. That is only the MTO (reactor I) and the MOI (reactor A) steps are carried out. Where the process is carried out to selectively produce distillate boiling range hydrocarbons the hydrocarbon effluent from the MOI reactor after separation of water and C$_2$− hydrocarbons is fed to the MOGD reactor operated under distillate conditions.

Reactor I (MTO)

A vaporized and/or liquid methanol feed containing less than 5% water, preferably less than 1% water is heated by means not shown and fed into line 51. The methanol feed is split into a first portion, fed to line 52 and a second portion fed to line 53.

The first portion contains about 50% of the methanol feed and is fed through line 52 to the fluid bed stage MTO reactor I. The methanol feed is fed at a 0.5 to 2 WHSV to reactor I.

The MTO fluid bed reactor I can be operated either in the preferred tubulent dense bed mode or as a dilute phase riser reactor. Exothermic heat of reaction is removed in an external cooling vessel not shown by circulating catalyst through transfer lines in a conventional manner. The conversion catalyst HZSM-5 is circulated continuously to a catalyst regeneration vessel, not shown.

The catalyst preferably contains 25% HZSM-5 catalyst and 75% alumina or silica carrier material.

The MTO reactor I is operated at a temperature of 482° to 527° C. (900° to 980° F.) and at a pressure of 170 to 273 kPa (10 to 25 psig). The MTO effluent product gas is withdrawn through line 54 and separated from any entrained catalyst in a gas-solids separator, not shown. The effluent product gas is taken through line 54, cooled by cooler 65 and is separated in crude separation vessel 66 into a by-product water stream withdrawn through line 56.

After separation of water, the reactor I hydrocarbon effluent has the following composition.

| | Wt. % |
|---|---|
| C$_2$− | 12 |
| C$_3$-C$_4$ | 52 |
| C$_5$-C$_9$ | 33[1] |
| C$_{10}$-C$_{20}$ | 3 |

[1] The aromatic content of the gasoline fraction is 12 wt. %, based on total hydrocarbons.

The methanol conversion to olefins is about 99.8%.

The separation vessel 66 separates the hydrocarbons into a C$_2$+ to C$_5$− olefin stream withdrawn through line 68 and a C$_3$ to C$_9$ olefin and aromatic hydrocarbon stream withdrawn through line 66a. The C$_3$ to C$_9$ hydrocarbon stream in line 66a is fed to gasoline splitter 67. A liquid C$_7$+ aromatic stream is withdrawn through line 67c and removed. A C$_6$− olefin hydrocarbon stream is withdrawn through line 67a and fed to compressor 67b by which its pressure is increased to about 1000 to 1480 kPa (130 to 200 psig) and is then fed through line 67a to line 70 and to the MOI intermediate reactor A. An alternative procedure, for example, where the end product is gasoline (removed through line 62a) the aromatic hydrocarbons are not separated and part or all of the C<sub>3</sub> to C<sub>9</sub> hydrocarbons are fed to compressor 67b and then to the MOI reactor.

The $C_2+$ to $C_5-$ hydrocarbons from crude separation vessel 66 are fed through line 68 to compressor 68a in which the pressure of the hydrocarbons is increased to 1000 to 1480 kPa (130 to 200 psig) and mixed with the $C_3$ to $C_9$ stream in line 67a and the second portion of the methanol feed in line 53 (comprising about 50% of the total methanol) and is fed through line 70 to the MOI (olefin interconversion) intermediate reactor A at a total feed rate of 0.4 to 4 WHSV and at a temperature of 316° to 343° C. (600° to 650° F.). Where the process is carried out to produce distillate, an ethene rich stream is separated in vessel 62 from the MOGD reactor II effluent and is recycled to the MOI reactor A through line 60 and fed to reactor A through line 70.

The mixed methanol, $C_2+$ olefin effluent hydrocarbons from reactor I and the ethene recycle stream from reactor II are contacted in reactor A with an HZSM-5 catalyst arranged in a dense fluidized bed reactor.

The intermediate reactor A is operated at a temperature of 316° to 343° C. (600° to 650° F.) and at a pressure of 1000 to 1480 kPa (130 to 200 psig).

The catalyst used comprises 25% HZSM-5 catalyst and 75% alumina binder.

The intermediate reactor A hydrocarbon effluent in line 62b, excluding water and any unconverted methanol that may be present, has the following composition.

|  | Wt. % |
|---|---|
| $C_2-$ | 7.6 |
| $C_3-C_4$ | 8.8 |
| $C_5-C_9$ | 65.6[1] |
| $C_{10}-C_{20}$ | 18.0 |

[1]The aromatic content of the gasoline fraction is 0 to 2 wt %, based on total hydrocarbons. The major portion of the aromatic hydrocarbons are separated and removed in the gasoline splitter 67 through line 67c.

The methanol conversion to olefins is about 96%.

If the process is carried out to selectively produce gasoline fraction hydrocarbons the process stops at this point with a yield of 65.6% $C_5$ to $C_9$ hydrocarbons being obtained. The gasoline product is removed through line 62a and taken to storage.

Comparison

The above product yields are compared with a conventional MTO/MOGD (gasoline mode) process in which all of the methanol feed is fed to the MTO reactor and the MTO $C_3+$ hydrocarbon effluent stream is fed to the MOGD reactor operated to selectively produce gasoline.

The reaction conditions for the typical conventional MTO/MOGD (gasoline mode) process in which the entire methanol feed is fed to the MTO reactor are summarized below.

Conventional MTO/MOGD (Gasoline Mode) Process

MTO Reactor
Methanol feed 0.1 to 1 WHSV
Temperature 482° to 527° C. (900° to 980° F.)
Pressure 101 to 308 pKa (0 to 30 psig)
The methanol conversion to olefins is about 99.9.
MOGD Reactor (Gasoline Mode)
Feed $C_3+$ olefin stream from MTO 0.1 to 2 WHSV
Temperature 315° to 400° C. (600° to 750° F.)
Pressure 4900 to 7000 kPa (700 to 1000 psig)
The conventional MTO aromatic make is typically 13 wt. % and the methanol conversion is typically 99.9 wt. %.

The comparison MTO/MOGD (gasoline mode) process effluent stream which is obtained is shown below with that of the invention MTO/MOI intermediate reactor A process effluent stream.

|  | Invention MTO/MOI Wt. % | Comparison Conventional MTO/MOGD (Gasoline Mode) Wt. % |
|---|---|---|
| $C_2-$ | 7.6[1] | 13.4[1] |
| $C_3-C_4$ | 8.8 | 12.0 |
| $C_5-C_9$ | 65.6[2] | 43.6[2] |
| $C_{10}-C_{20}$ | 18.0 | 31.0 |

[1]The $C_2-$ stream is removed from the MTO reactors effluent in each case and is included here to show the overall material balance.
[2]The aromatics would normally be removed from the respective MTO effluents and would, based on total hydrocarbons in the gasoline product fraction, typically be 0-2 wt. % in each case.

The methanol conversion in the conventional MTO reactor process is typically 99.9%.

The MTO reactors in both the inventive process and the comparison process operate at higher temperatures than applicant's MOI reactor. The higher temperature operation of the MTO reactor results in the conversion of a portion of the methanol feed to aromatic hydrocarbons and to $C_2$ light gas. In accordance with applicant's invention, in which the methanol feed is split, with about half going to the MTO reactor and the other half going to the MOI reactor, the overall amount of aromatic hydrocarbons and $C_2$ light gas produced are significantly reduced.

The aromatic content of the invention MTO reactor effluent in this example is 12 wt. % compared to 13 wt. % for the conventional MTO process. The invention process $C_2$ light gas production is 7.6 wt. % compared to 13.4 wt. % for the conventional MTO/MOGD process.

Further, if applicant's entire methanol feed were fed to applicant's invention MTO reactor, the size of the MTO reactor and the investment needed for the MTO reactor would have to be about twice as large.

The information reported in the above table shows that the invention process by comparison produces less aromatics and less $C_2-$ olefins and substantially more of the desired $C_5$ to $C_9$ gasoline fraction.

If the process is carried out to selectively produce distillate fraction hydrocarbons, the MOI intermediate reactor A effluent is fed to the MOGD reactor II (distillate mode). In accordance with this embodiment of the invention, the intermediate reactor A effluent product hydrocarbons are withdrawn through line 62b, cooled in cooling means 74 and fed through line 62b into separator vessel 69.

In the separator vessel 69, water and any unreacted methanol are removed through line 64. An overhead $C_2-$ stream is removed through line 63 and fed to deethanizer absorber tower 70. A bottom $C_3+$ stream is withdrawn from separator vessel 69 through line 72 and is fed to deethanizer absorber tower 70. A portion of the $C_5$–$C_9$ gasoline product stream withdrawn in line 58 from the separation means 62 is recycled through line 75 to the deethanizer absorber tower 70. In the tower 70 the $C_5$–$C_9$ gasoline recycle stream absorbs $C_2+$ hydrocarbons from the $C_2-$ hydrocarbon stream fed to tower 70 through line 63. An overhead $C_2-$ fuel gas stream is removed through line 55. The $C_5$–$C_9$ gasoline stream with absorbed $C_2+$ hydrocarbons is mixed with the $C_3+$ hydrocarbon stream fed to tower 70 through line 72 and a $C_3+$ hydrocarbon stream is withdrawn from the tower 70 through line 73.

The $C_3+$ hydrocarbon stream in line 73 is fed to compressor 71 in which its pressure is increased to 5600 to 7000 kPa (800 to 1000 psig) and is then fed through line 73a to the MOGD reactor II at 0.4 to 4.0 WHSV. The feed to the MOGD reactor includes a 1:1 weight ratio recycle of the $C_5$–$C_9$ gasoline stream fed through lines 58 and 75.

The $C_3+$ hydrocarbons are contacted in the reactor II with HZSM-5 catalyst in a multistage fixed bed reactor having three stages. The reactor II is operated under conditions to optimize distillate product at a pressure of 5600 to 7000 pKa (800 to 1000 psig) and at a temperature of 232° to 343° C. (450° to 650° F.).

The catalyst comprises 65% HZSM-5 catalyst and 35% alumina carrier operated in a three stage fixed bed reactor.

The reactor II effluent hydrocarbon product is withdrawn through line 55, cooled by means not shown and is fed to separation means 62.

A portion of the $C_5$–$C_9$ gasoline stream is, as discussed above, recycled through lines 58 and 75 to the deethanizer absorber tower 70.

After separation of any water that may be present, through line 61, the reactor II hydrocarbon effluent in line 55 has the following composition.

|  | Wt. % |
|---|---|
| $C_2-$ | 7.6 |
| $C_3$–$C_4$ | 9.3 |
| $C_5$–$C_9$[1] | 30.1 |
| $C_{10}$–$C_{20}$ | 53.0 |

[1] The aromatic content of the gasoline fraction is less than 1 wt. %, based on total hydrocarbons.

The $C_3$–$C_4$ (LPG) stream is removed through line 57, the $C_5$–$C_9$ stream (less recycle) is removed through line 58 and the $C_{10}$–$C_{20}$ distillate stream is removed through line 59.

For comparison purposes the conventional MTO/MOGD (distillate mode) process is carried out. The product yields of the invention MTO/MOI/MOGD (distillate mode) process are compared with the product yields obtained in the conventional MTO/MOGD distillate mode process.

The reaction conditions for the conventional MTO/MOGD (distillate mode) process are summarized below.

Conventional MTO/MOGD (Distillate Mode) Process

| Conventional MTO/MOGD (Distillate Mode) Process | |
|---|---|
| MTO Reactor | |
| Methanol Feed | 0.1 to 1 WHSV |
| Temperature | 482 to 527° C. to (900 to 980° F.) |

| -continued | |
|---|---|
| Conventional MTO/MOGD (Distillate Mode) Process | |
| Pressure | 101 to 300 kPa (0 to 30 psig) |
| The methanol conversion to olefins is about 99.9 wt. %. | |
| MOGD Reactor (Distillate Mode) | |
| Feed $C_3+$ olefin stream from MTO | 0.1 to 2 WHSV |
| Temperature | 204 to 343° C. (400 to 650° F.) |
| Pressure | 4900 to 700 kPa (700 to 1000 psig) |

The conventional MTO methanol conversion is typically 99.9%.

The MTO/MOGD effluent stream (comparison) that is obtained is shown below with that of the MTO/MOI/MOGD effluent stream (invention).

|  | Invention MTO/MOI/MOGD Wt. % | Comparison Conventional MTO/MOGD Distillate Mode) Wt.% |
|---|---|---|
| $C_2-$ | 7.6[1] | 13.4[1] |
| $C_3$–$C_4$ | 9.3 | 12.3 |
| $C_5$–$C_9$ | 30.1[2] | 25.6[2] |
| $C_{10}$–$C_{20}$ | 53.0 | 48.7 |

[1] The $C_2-$ stream is removed from the MTO reaction effluent in each case and is included here to show the overall material balance.

The information reported in the above table shows that the invention process by comparison produces less aromatics, less $C_2-$ light gas and less $C_3$–$C_4$ hydrocarbons and significantly more of the desired $C_{10}$–$C_{20}$ distillate hydrocarbons and gasoline hydrocarbons.

The above Examples 1 and 2 illustrate that using the prior art process of feeding all of the methanol feed to the MTO reactor I results in the production of more $C_2$ light gas and in the production of more aromatic hydrocarbons, both of which decrease the overall desired gasoline and heavy distillate production, respectively. In addition, additional aromatics removal capacity is required to remove the relatively larger amount of aromatics from the MTO effluent hydrocarbon product, since it is preferred not to have too large amount of aromatics in the gasoline product and to not have any significant amount of aromatics in the heavy distillate product.

The foregoing description of the present invention has omitted various heating and cooling apparatus, catalyst regenerators, compressors and like equipment which are conventional and well known to those skilled in the art. Further, recycle streams other than those described can be utilized to optimize specifically desired process streams.

The described integrated processes provide effective means for converting oxygenated organic compounds such as methanol, DME, lower aliphatic ketones and aldehydes to valuable hydrocarbon products. Thermal integration is achieved by employing heating and cooling means between various process streams, towers, absorbers, etc., in a conventional manner.

Various modifications can be made to the systems, especially in the choice of equipment and non-critical processing steps. While the invention has been described by specific examples, there is no intent to limit the inventive concept except as set forth in the following claims.

What is claimed is:

1. An integrated process for converting an oxygenate feed to selectively produce distillate range liquid hydrocarbons which consists essentially of the steps of
    splitting the oxygenate feed into two portions,
    contacting a first 60 to 40% portion of the oxygenate feed with a zeolite catalyst in a MTO first reactor at elevated temperature of 800° to 950° F. and moderate pressure of 10 to 80 psig to covert at least 80 wt. % of the oxygenate feed and recovering an effluent comprising $C_2-$ and $C_3+$ olefin hydrocarbons and by-product water,
    cooling the effluent from the MTO first reactor and separating a $C_2-$ olefin hydrocarbon stream, a $C_3$ to $C_9$ hydrocarbon stream containing $C_5-C_9$ aromatic hydrocarbons, and by-product water,
    removing the $C_5-C_9$ aromatic hydrocarbons from the $C_3$ to $C_9$ stream to obtain a $C_3$ to $C_9$ olefin hydrocarbon stream,
    contacting a second 40 to 60% portion of the oxygenate feed and the entire $C_3$ to $C_9$ olefin hydrocarbon stream from the MTO first reactor in a MOGD second reactor with an oligomerization zeolite catalyst at moderate temperature of 400° to 650° F. and substantially increased pressure of 600 to 1500 psig under oligomerization reaction conditions to selectively convert at least 50 wt. % of the oxygenate feed and the $C_3$ to $C_9$ olefin hydrocarbons to distillate range hydrocarbons and by-product water, and
    cooling the effluent from the MOGD second reactor and separating hydrocarbons containing a high concentration of distillate range liquid hydrocarbons from the by-product water.

2. The integrated process of claim 1 wherein the hydrocarbon effluent from the MOGD second reactor, after removal of by-product water contains 60–75 wt. % $C_{10}$ to $C_{20}$ distillate hydrocarbons.

3. An integrated process for converting an oxygenate feed to selectively produce gasoline range liquid hydrocarbons which consists essentially of the steps of
    splitting the oxygenate feed into two portions,
    contacting a first 60 to 40% portion of the oxygenate feed with a zeolite catalyst in a MTO first reactor at elevated temperature of 800° to 950° F. and moderate pressure of 10 to 80 psig to convert at least 80 wt. % of the oxygenate feed to $C_2+$ olefin hydrocarbons and recovering an effluent comprising $C_2+$ olefin hydrocarbons and by-product water,
    cooling the effluent from the MTO first reactor and separating a $C_2$ to $C_9$ hydrocarbon stream containing $C_5-C_9$ aromatic hydrocarbons, and by-product water,
    contacting a second 40 to 60% portion of the oxygenate feed and the entire $C_2$ to $C_9$ hydrocarbon stream, including the $C_5-C_9$ aromatic hydrocarbons, from the MTO first reactor in a MOI intermediate reactor with a zeolite catalyst at moderate temperature of 550° to 700° F. and a pressure of 100 to 250 psig to selectively convert at least 50% of the oxygenate feed and the $C_2$ to $C_9$ olefins to gasoline range liquid hydrocarbons comprising $C_2-$ and $C_3+$ olefins and by-product water,
    cooling the effluent from the MOI intermediate reactor and separating a $C_2-$ olefin containing hydrocarbon stream, a $C_3+$ olefin hydrocarbon stream containing a high concentration of gasoline range liquid hydrocarbons and by-product water.

4. The integrated process of claim 3 wherein the hydrocarbon effluent from the MOI intermediate reactor after removal of by-product water contains 35–70 wt. % of $C_5-C_9$ gasoline range liquid hydrocarbons.

5. An integrated process for converting an oxygenate feed comprising methanol, dimethyl ether or mixtures thereof to selectively produce distillate range liquid hydrocarbons which consists essentially of the steps of
    splitting the oxygenate feed into two portions,
    contacting a first 60 to 40% potion of the oxygenate feed with a zeolite catalyst in a MTO first reactor at elevated temperature of 800° to 950° F. and moderate pressure of 10 to 80 psig to convert at least 80 wt. % of the oxygenate feed to $C_2+$ olefin hydrocarbons and by-product water,
    cooling the effluent from the MTO first reactor and separating a $C_2$ to $C_9$ hydrocarbon stream containing $C_5-C_9$ aromatic hydrocarbons, and by-product water,
    removing the $C_5-C_9$ aromatic hydrocarbons from the $C_2$ to $C_9$ hydrocarbon stream to obtain a $C_2$ to $C_9$ olefin hydrocarbon stream,
    contacting a second 40 to 60% portion of the oxygenate feed and the entire $C_2$ to $C_9$ olefin hydrocarbon stream from the MTO first reactor in a MOI intermediate reactor with a zeolite catalyst at moderate temperature of 550° to 700° F. and at a pressure of 100 to 250 psig to convert at least 50 wt. % of the oxygenate feed and the $C_2$ to $C_9$ olefins to heavier hydrocarbons comprising $C_2-$ and $C_3+$ olefins and by-product water,
    cooling the effluent from the MOI intermediate reactor and separating a $C_2-$ olefin hydrocarbon stream, a $C_3$ to $C_{20}$ olefin hydrocarbon stream and by-product water,
    contacting the $C_3$ to $C_{20}$ hydrocarbon stream in a MOGD second reactor with an oligomerization zeolite catalyst at moderate temperature of 400° to 650° F. and increased pressure of 600 to 1500 psig under oligomerization reaction conditions to selectively convert the $C_3$ to $C_{20}$ hydrocarbons to distillate range liquid hydrocarbons.

6. The integrated process of claim 5 wherein the effluent from the MOGD second reactor after removal of water contains 20 to 65 wt. % of $C_{10}-C_{20}$ distillate hydrocarbons.

* * * * *